(12) United States Patent
Li et al.

(10) Patent No.: US 9,062,006 B2
(45) Date of Patent: Jun. 23, 2015

(54) HIGH MOLECULAR WEIGHT POLYLACTIC ACID SYNTHESIZED VIA POLYCONDENSATION CATALYZED BY BIONIC CREATININE GUANIDINIUM CHLORIDE

(75) Inventors: Hong Li, Jiangsu (CN); Quanxing Zhang, Jiangsu (CN); Wei Huang, Jiangsu (CN); Wei Jiang, Jiangsu (CN); Xupeng Zong, Jiangsu (CN); Bingcai Pan, Jiangsu (CN)

(73) Assignee: NANJING UNIVERSITY, Nanjing (CN)

( * ) Notice: Subject to any disclaimer, the term of this patent is extended or adjusted under 35 U.S.C. 154(b) by 28 days.

(21) Appl. No.: 14/129,323

(22) PCT Filed: Nov. 2, 2011

(86) PCT No.: PCT/CN2011/081700
§ 371 (c)(1),
(2), (4) Date: Dec. 26, 2013

(87) PCT Pub. No.: WO2013/000226
PCT Pub. Date: Jan. 3, 2013

(65) Prior Publication Data
US 2014/0121347 A1    May 1, 2014

(30) Foreign Application Priority Data

Jun. 30, 2011 (CN) .......................... 2011 1 0181170

(51) Int. Cl.
| | |
|---|---|
| *C08G 63/87* | (2006.01) |
| *C07D 233/50* | (2006.01) |
| *A61L 27/18* | (2006.01) |
| *A61L 31/06* | (2006.01) |
| *A61K 47/34* | (2006.01) |
| *A61L 17/12* | (2006.01) |
| *C07D 233/32* | (2006.01) |
| *C08G 63/06* | (2006.01) |

(52) U.S. Cl.
CPC ............... *C07D 233/50* (2013.01); *A61L 27/18* (2013.01); *A61L 31/06* (2013.01); *A61K 47/34* (2013.01); *A61L 17/12* (2013.01); *C07D 233/32* (2013.01); *C08G 63/06* (2013.01); *C08G 63/87* (2013.01)

(58) Field of Classification Search
None
See application file for complete search history.

(56) References Cited

U.S. PATENT DOCUMENTS

| | | | | |
|---|---|---|---|---|
| 4,677,191 | A | * | 6/1987 | Tanaka et al. ................. 528/361 |
| 4,683,288 | A | * | 7/1987 | Tanaka et al. ................. 528/361 |
| 2014/0142275 | A1 | * | 5/2014 | Li et al. ......................... 528/361 |

FOREIGN PATENT DOCUMENTS

| | | |
|---|---|---|
| CN | 1556128 | 12/2004 |
| CN | 1786042 | 6/2006 |
| CN | 101215263 | 7/2008 |
| CN | 101215374 | 7/2008 |
| CN | 101215374 A | 7/2008 |
| CN | 102161752 | 8/2011 |

OTHER PUBLICATIONS

International Search Report filed in PCT/CN2011/081700, Mar. 22, 2012.
Treat B. Johnson et al., Researches on Hydantoins. XXXV. A New Method of Synthesizing Glycocyamidine Compounds, and the Conversion of Glycocyamidine Into Isomers of Creatinine, Journal American Chemical Society, vol. 37, pp. 2416-2426, Dec. 31, 1915, New Haven, Connecticut.

* cited by examiner

*Primary Examiner* — Monica Huson
(74) *Attorney, Agent, or Firm* — Rankin, Hill & Clark LLP

(57) ABSTRACT

Disclosed is a high molecular weight polylactic acid synthesized by using a method for synthesizing and catalytically-polycondensing bionic creatinine-guanidinium chloride. Creatinine is used as the material in a reaction with aqueous hydrochloric acid to synthesize a bionic creatinine-guanidinium salt catalyst, creatinine-guanidinium chloride (CR.Cl). The creatinine-guanidinium chloride synthesized is used as a catalyst, an industrial grade lactic acid (LA, 85% to 90%, aqueous solution) is used as a monomer, a solvent-free two-step polycondensation method is used to synthesize and afford metal-free and toxic residue-free polylactic acid featuring high biological safety and high molecular weight.

2 Claims, No Drawings

HIGH MOLECULAR WEIGHT POLYLACTIC ACID SYNTHESIZED VIA POLYCONDENSATION CATALYZED BY BIONIC CREATININE GUANIDINIUM CHLORIDE

FIELD OF THE INVENTION

The present invention belongs to the field of biodegradable medical materials, relating to a process for synthesizing polylactic acid featuring a high biological safety and a high molecular weight via polycondensation, wherein a bionic organic guanidinium salt, creatinine-guanidinium chloride, is used as catalyst.

BACKGROUND OF THE INVENTION

In recent years, along with the rapid development of medicine, pharmacy and biological tissue engineering, the demand for materials featuring good biocompatibility, biological safety and biodegradability is rapidly growing throughout the world. Biodegradable polylactic acid has been extensively applied in modern pharmaceutical science (controlled-released and targeted drug carriers), biological tissue engineering science (surgical sutures, bone screws, fracture splints, meniscus-repairing materials and devices, cells and bioactive species scaffold materials) and the like. It is required that the polymers used in the field of pharmacy and medicine should not contain any metal and toxic ingredient. Currently, the production of commercially available polylactic acid is mainly performed as follows: 1. ring-opening polymerization of lactide catalyzed by stannous octoate; 2. polycondensation of lactic acid catalyzed by stannous chloride. Although both methods can synthesize a polymer with desired molecular weight, the tin salt catalyst cannot be completely removed from the polymer after polymerization. In recent years, by the studies of scientists worldwide, it has been definitely proved that both stannous octoate and stannous chloride exhibit cytotoxicity. Therefore, the safety issue of polylactic acid for pharmaceutical and medical materials for human, synthesized by using stannous octoate or stannous chloride as catalyst, has been extensively questioned by scientists all over the world. The exploration for efficient, non-toxic, and metal-free catalysts for synthesizing metal-free, non-toxic, and highly biologically safe polylactic acid materials for medical and pharmaceutical applications has become the urgent issue proposed by scientists in the field of biomaterial science throughout the world.

Based on the invention of domestic scholars such as Professor LI Hong and the co-workers, wherein the non-toxic, metal-free and highly biologically safe polylactic acid was successively synthesized via direct polycondensation catalyzed by creatinine (Mw=1.5~3.0×10$^4$) (Chinese Patent Application: 201110059090.8), the present invention employs bionic organic catalyst firstly developed, creatinine-guanidinium chloride, to provide a process for synthesizing polylactic acid with a high molecular weight for medical and pharmaceutical purposes via direct polycondensation of lactic acid.

SUMMARY OF THE INVENTION

The object of the present invention is to solve the potential safety problem caused by the high molecular weight polylactic acid, synthesized via polycondensation by stannous chloride-catalyzed, for human medical material application, and to provide a process for synthesizing biodegradable medical polylactic acid featuring a high molecular weight and a high biological safety via direct polycondensation by using a non-toxic, metal-free, and bionic organic guanidinium compound as catalyst.

1. For the first time, the present invention develops non-toxic, metal-free bionic organic guanidinium salt, i.e. creatinine-guanidinium chloride (CR.Cl). The synthetic process thereof uses creatinine (CR, a biomass organic guanidinium compound, a metabolite of arginine in human body) as raw material to react with aqueous hydrochloric acid. The synthetic process is performed under selected process conditions, and the scheme of the synthetic process is shown as follows:

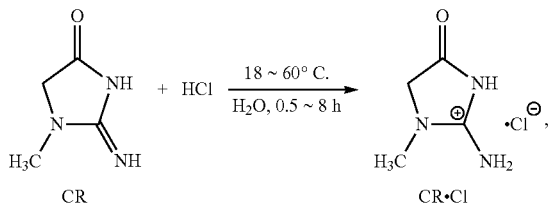

Synthetic conditions: temperature: 18~60° C.; Time: 0.5~8 h; the molar ratio between creatinine and hydrochloric acid: 1:1~1.2.

Synthetic steps: to a Schlenk reactor, 30~40 mL of deionized water was added, followed by 5 g (44.3 mmol) of creatinine. Under a high-purity argon atmosphere, the mixture was heated with stirring. After the temperature in reactor reached up to the predetermined temperature (18~60° C., e.g. 25° C.), a 18.5 wt % hydrochloric acid aqueous solution was added via a constant pressure dropping funnel. The molar ratio between creatinine and hydrochloride was adjusted as 1:1~1.2. The reaction was kept with stirring for a certain period of time (0.5~8 h, e.g. 2 h).

2. The present invention also provides a process for synthesizing biodegradable medical polylactic acid (PLA) featuring a high molecular weight via direct polycondensation of lactic acid (LA) catalyzed by creatinine-guanidinium chloride catalyst as synthesized above. In this process, the non-toxic, metal-free creatinine-guanidinium chloride as synthesized above is used as a catalyst, an aqueous solution of industrial grade lactic acid with a mass percentage of 85~90% is used as a monomer, a solvent-free two-step polycondensation method is used to synthesize and obtain a metal-free, non-toxic polylactic acid featuring a high biological safety and a high molecular weight. The steps thereof are shown as follows:

Synthetic Routes:

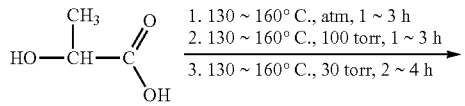

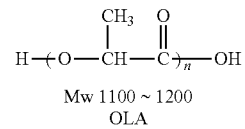

Mw 1100 ~ 1200
OLA

-continued

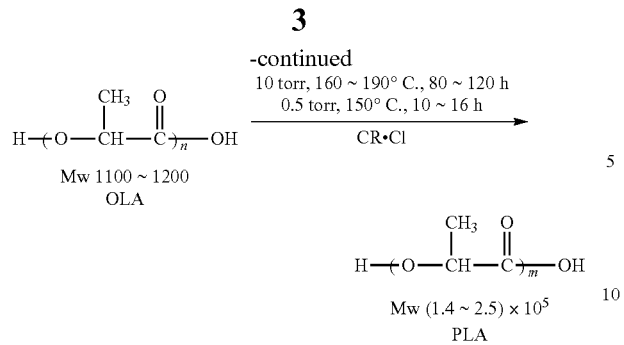

Synthetic Steps:

1. First-step polycondensation: synthesis of oligolactic acid (OLA) with a weight average molecular weight of 110~1200 by autocatalysis An aqueous solution of industrial grade lactic acid with a mass percentage of 85~90% was used, as a monomer, to firstly synthesize an oligolactic acid, wherein the weight average Mw=1100~1200; Synthetic conditions: a reactor was charged with lactic acid, and then vacuumized and charged with argon for three repetitions; Under an argon atmosphere at normal pressure, the reaction system was heated to 130~160° C. and subjected to dehydration for 1~3 h; The pressure in the reactor was then reduced to 100 Torr, reacting at 130~160° C. for 1~3 h; Finally, the pressure in the reactor was reduced to 30 Torr, reacting at 130~160° C. for 2~4 h;

2. Two-step polycondensation: synthesis of high molecular weight polylactic acid (PLA) via melt polycondensation of oligolactic acid (OLA) catalyzed by creatinine-guanidine chloride.

The oligolactic acid OLA synthesized in the first step, first-step polycondensation, was used as raw material; the bionic creatinine-guanidinium chloride synthesized by the process mentioned above was used as a catalyst; Under a reduce pressure, the melt polycondensation was performed to synthesize medical and pharmaceutical polylactic acid featuring a high molecular weight and a high biological safety; The process conditions and operation methods of synthetic reaction were described as follows:

Oligolactic acid and creatinine-guanidinium chloride catalyst were added into the reactor; The mass ratio between creatinine-guanidinium chloride and oligolactic acid was set as 1:100~1:1000; The pressure in the reactor was reduced to 10 Torr, heating to 160~190° C. for 80~120 h; Finally, the pressure in the reactor was reduced to 0.5 torr, reacting at 150° C. for 10~16 h.

The high molecular weight polylactic acid synthesized in the present invention has a weight average molecular weight Mw=1.4~2.5×10$^5$. The polylactic acid synthesized does not contain any metal and other toxic ingredients and thus can be applied in the field of modern pharmaceutical science (controlled-released and targeted drug carriers, etc.), medical science, and biological tissue engineering science (surgical sutures, bone screws, fracture splints, meniscus-repairing materials and devices, cells and bioactive species scaffold materials).

The advantages and beneficial effects of the present invention are as follows:

1. The creatinine-guanidinium chloride used exhibits high biocompatibility, biological safety;
2. The synthesized product, high molecular weight polylactic acid (Mw=1.4~2.5×10$^5$), does not contain any metal and other toxic ingredients, and thus can be suitable for applying in the field of medicine and pharmacy for human;
3. Entire green technology—green catalyst, polymerization without using any solvent, no occurrence of toxic products, highly biologically safe and biodegradable polylactic acid product;
4. Low cost of raw materials, simple technical operation, easy for industrial practice.

DETAILED DESCRIPTION OF THE EMBODIMENTS

Example 1

Synthesis of Creatinine-Guanidinium Chloride

To a Schlenk reactor, 30 mL of deionized water was added, followed by 5 g (44.3 mmol) of creatinine. Under a high-purity argon atmosphere, the mixture was heated with stirring. After the temperature in reactor reached up to the predetermined temperature of 18° C., an aqueous solution of hydrochloric acid at a concentration of 18.5% was added via a constant pressure dropping funnel into the reactor. The molar ratio between creatinine and hydrochloride was set as 1:1. The reaction was kept with stirring for 8 h. By using a rotary evaporator, the moisture contained in the system was removed under reduced pressure. The solid product was transferred into a vacuum oven and dried at room temperature for 48 h, to give 6.48 g of creatinine-guanidinium chloride as a snow white solid product.

Example 2

Synthesis of Creatinine-Guanidinium Chloride

To a Schlenk reactor, 40 mL of deionized water was added, followed by 5 g (44.3 mmol) of creatinine. Under a high-purity argon atmosphere, the mixture was heated with stirring. After the temperature in reactor reached up to the predetermined temperature of 60° C., an aqueous solution of hydrochloric acid at a concentration of 18.5% was added via a constant pressure dropping funnel into the reactor. The molar ratio between creatinine and hydrochloride was set as 1:1.2. The reaction was kept with stirring for 0.5 h. By using a rotary evaporator, the moisture contained in the system was removed under reduced pressure. The solid product was transferred into a vacuum oven and dried at room temperature for 48 h, to give 6.58 g of creatinine-guanidinium chloride as a snow white solid product.

Example 3

Synthesis of Creatinine-Guanidinium Chloride

To a Schlenk reactor, 30 mL of deionized water was added, followed by 5 g (44.3 mmol) of creatinine. Under a high-purity argon atmosphere, the mixture was heated with stirring. After the temperature in reactor reached up to the predetermined temperature of 60° C., an aqueous solution of hydrochloric acid at a concentration of 18.5% was added via a constant pressure dropping funnel into the reactor. The molar ratio between creatinine and hydrochloride was set as 1:1.1. The reaction was kept with stirring for 4 h. By using a rotary evaporator, the moisture contained in the system was removed under reduced pressure. The solid product was transferred into a vacuum oven and dried at room temperature for 48 h, to give 6.52 g of creatinine-guanidinium chloride as a snow white solid product.

Example 4

Synthesis of Oligolactic Acid

A reactor was charged with 100 g of L-lactic acid (featuring a mass percentage of 85~90%), and then vacuumized and charged with argon for three repetitions. Under an argon atmosphere at normal pressure, the reaction system was then heated to 130° C. and subjected to dehydration for 3 h. The pressure in the reactor was then reduced to 100 Torr, reacting at 130° C. for 3 h. Finally, the pressure in the reactor was reduced to 30 Torr, reacting at 130° C. for 4 h, to give 82 g of oligolactic acid (OLA), with a weight average molecular weight of 1100 as determined by GPC.

Example 5

Synthesis of Oligolactic Acid

A reactor was charged with 100 g of L-lactic acid (featuring a mass percentage of 85~90%), and then vacuumized and charged with argon for three repetitions. Under an argon atmosphere at normal pressure, the reaction system was then heated to 160° C. and subjected to dehydration for 1 h. The pressure in the reactor was then reduced to 100 Torr, reacting at 160° C. for 1 h. Finally, the pressure in the reactor was reduced to 30 Torr, reacting at 160° C. for 2 h, to give 84 g of oligolactic acid (OLA), with a weight average molecular weight of 1200 as determined by GPC.

Example 6

Synthesis of Oligolactic Acid

A reactor was charged with 100 g of L-lactic acid (featuring a mass percentage of 85~90%), and then vacuumized and charged with argon for three repetitions. Under an argon atmosphere at normal pressure, the reaction system was then heated to 145° C. and subjected to dehydration for 2 h. The pressure in the reactor was then reduced to 100 Torr, reacting at 145° C. for 2 h. Finally, the pressure in the reactor was reduced to 30 Torr, reacting at 145° C. for 3 h, to give 82 g of oligolactic acid (OLA), with a weight average molecular weight of 1130 as determined by GPC.

Example 7

Synthesis of High Molecular Weight Polylactic Acid 50 g of oligolactic acid (OLA) (Mw 1100) and 200 mg of creatinine-guanidinium chloride catalyst were added into the reactor. The pressure in the reactor was reduced to 10 Torr, heating the reaction to 160° C. for 120 h. Finally, the pressure in the reactor was reduced to 0.5 torr, reacting at 150° C. for 16 h. After stopping the reaction, the reactor was cooled to room temperature. The polymer was dissolved in acetone, and then poured into water at 0° C. to be precipitate. The mixture was filtered under reduced pressure, and the solid was dried under vacuum at 30° C. for 48 h, to give a silver white solid. The result measured by GPC showed that the weight average molecular weight $Mw=1.4\times10^5$. Yield: 84.5%.

Example 8

Synthesis of High Molecular Weight Polylactic Acid 50 g of oligolactic acid (OLA) (Mw 1100) and 200 mg of creatinine-guanidinium chloride catalyst were added into the reactor. The pressure in the reactor was reduced to 10 Torr, heating the reaction to 190° C. for 80 h. Finally, the pressure in the reactor was reduced to 0.5 torr, reacting at 150° C. for 12 h. After stopping the reaction, the reactor was cooled to room temperature. The polymer was dissolved in acetone, and then poured into water at 0° C. to be precipitate. The mixture was filtered under reduced pressure, and the solid was dried under vacuum at 30° C. for 48 h, to give a silver white solid. The result measured by GPC showed that the weight average molecular weight $Mw=2.5\times10^5$. Yield: 81.6%.

Example 9

Synthesis of High Molecular Weight Polylactic Acid 50 g of oligolactic acid (OLA) (Mw 1100) and 200 mg of creatinine-guanidinium chloride catalyst were added into the reactor. The pressure in the reactor was reduced to 10 Torr, heating the reaction to 175° C. for 100 h. Finally, the pressure in the reactor was reduced to 0.5 torr, reacting at 150° C. for 10 h. After stopping the reaction, the reactor was cooled to room temperature. The polymer was dissolved in acetone, and then poured into water at 0° C. to be precipitate. The mixture was filtered under reduced pressure, and the solid was dried under vacuum at 30° C. for 48 h, to give a silver white solid. The result measured by GPC showed that the weight average molecular weight $Mw=2.0\times10^5$. Yield: 82.3%.

Example 10

Synthesis of High Molecular Weight Polylactic Acid 50 g of oligolactic acid (OLA) (Mw 1100) and 500 mg of creatinine-guanidinium chloride catalyst were added into the reactor. The pressure in the reactor was reduced to 10 Torr, heating the reaction to 180° C. for 100 h. Finally, the pressure in the reactor was reduced to 0.5 torr, reacting at 150° C. for 10 h. After stopping the reaction, the reactor was cooled to room temperature. The polymer was dissolved in acetone, and then poured into water at 0° C. to be precipitate. The mixture was filtered under reduced pressure, and the solid was dried under vacuum at 30° C. for 48 h, to give a silver white solid. The result measured by GPC showed that the weight average molecular weight $Mw=2.2\times10^5$. Yield: 83.0%.

Example 10

Synthesis of High Molecular Weight Polylactic Acid 50 g of oligolactic acid (OLA) (Mw 1100) and 50 mg of creatinine-guanidinium chloride catalyst were added into the reactor. The pressure in the reactor was reduced to 10 Torr, heating the reaction to 160° C. for 120 h. Finally, the pressure in the reactor was reduced to 0.5 torr, reacting at 150° C. for 10 h. After stopping the reaction, the reactor was cooled to room temperature. The polymer was dissolved in acetone, and then poured into water at 0° C. to be precipitate. The mixture was filtered under reduced pressure, and the solid was dried under vacuum at 30° C. for 48 h, to give a silver white solid. The result measured by GPC showed that the weight average molecular weight $Mw=1.1\times10^5$. Yield: 84.1%.

What is claimed is:

1. A method of making a high molecular weight polylactic acid (PLA) that is free of intentionally added tin salt catalysts, the method comprising:

autocatalytically reacting an industrial grade lactic acid (LA) comprising an aqueous solution of about 85 mass percent to about 90 mass percent lactic acid, in a polycondensation reaction as represented by the following chemical equation,

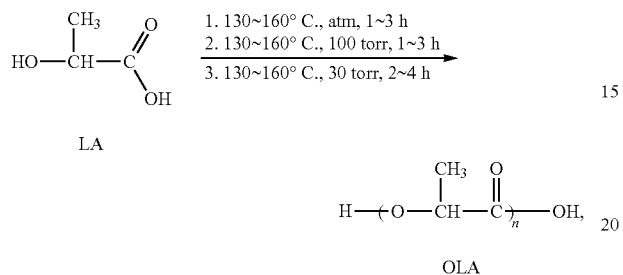

the polycondensation reaction comprising:
i) heating the industrial grade lactic acid from about 130° C. to about 160° C. for about 1 hour to about 3 hours, in an argon atmosphere at normal pressure,
ii) heating the industrial grade lactic acid from about 130° C. to about 160° C. for about 1 hour to about 3 hours, in an argon atmosphere at a pressure of about 100 Torr, and
iii) heating the industrial grade lactic acid from about 130° C. to about 160° C. for about 2 hours to about 4 hours, in an argon atmosphere at a pressure of about 30 Torr,
to thereby make oligolactic acid (OLA) having a weight average molecular weight of from about 1100 to about 1200; and reacting the oligolactic acid (OLA) and creatinine-guanidinium chloride (CR.Cl) in a mass ratio between creatinine-guanidinium chloride (CR.Cl) and oligolactic acid (OLA) from about 1:100 to about 1:1000, in a two-step solvent-free melt polycondensation reaction as represented by the following chemical equation,

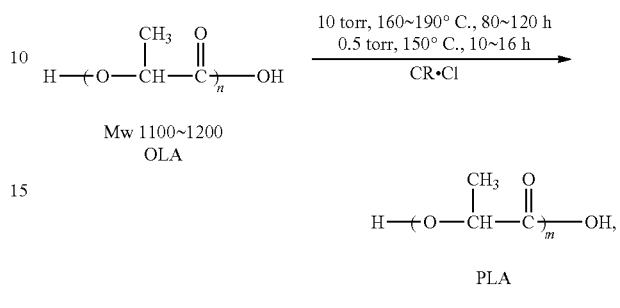

the two-step solvent-free melt polycondensation reaction comprising:
a) heating the oligolactic acid and the creatinine-guanidinium chloride to a temperature of from about 160° C. to about 190° C. for about 80 hours to about 120 hours, at a pressure of about 10 Torr, and
b) heating the oligolactic acid and the creatinine-guanidinium chloride to a temperature of about 150° C. for about 10 hours to about 16 hours, at a pressure of 0.5 Torr,
to thereby make the high molecular weight polylactic acid (PLA) that is free of intentionally added tin salt catalysts.

2. The method according to claim 1, wherein the high molecular weight polylactic acid has a weight average molecular weight (Mw) of from about $1.4 \times 10^5$ to about $2.5 \times 10^5$.

* * * * *